United States Patent [19]

Murthy et al.

[11] Patent Number: 5,508,423
[45] Date of Patent: Apr. 16, 1996

[54] METHODS FOR THE MANUFACTURE OF FLUCONAZOLE

[75] Inventors: Keshava Murthy; Gamini Weeratunga, both of Brantford; Derek J. Norris, Oakville; Bruno K. Radatus, Brantford, all of Canada

[73] Assignee: ACIC (Canada) Inc., Brantford, Canada

[21] Appl. No.: 459,226

[22] Filed: Jun. 2, 1995

[51] Int. Cl.$^6$ .................................................. C07D 403/06
[52] U.S. Cl. ........................................................ 548/266.6
[58] Field of Search ........................................... 548/266.6

[56] References Cited

U.S. PATENT DOCUMENTS

| | | | |
|---|---|---|---|
| 4,404,216 | 9/1983 | Richardson et al. | 548/266.6 |
| 4,560,697 | 12/1985 | Richardson et al. | 548/266.6 |

Primary Examiner—Patricia L. Morris
Attorney, Agent, or Firm—Ivor M. Hughes; Neil H. Hughes; Marcelo K. Sarkis

[57] ABSTRACT

A process for making Fluconazole comprising the steps of:

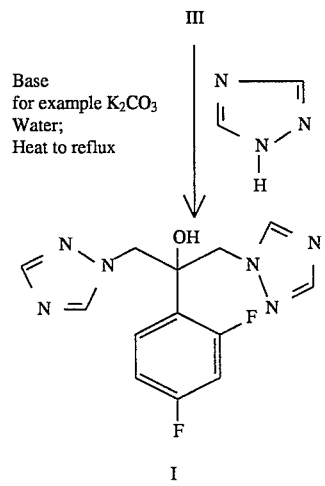

4 Claims, No Drawings

METHODS FOR THE MANUFACTURE OF FLUCONAZOLE

FIELD OF INVENTION

This invention relates to a novel process for the manufacture of Fluconazole.

BACKGROUND OF THE INVENTION

Fluconazole,α-(2,4-Difluorophenyl)-α-(1H-1,2,4,-triazole-1-ylmethyl)-1H-1,2,4-triazole-1-ethanol; 2,4-Difluoro-α-α-bis(1H-1,2,4-triazol-1-ylmethyl)benzyl alcohol; 2-(2,4-Difluorophenyl)-1,3-bis(1H-1,2,4-triazol-1-yl)-propan-2-ol, is an antifungal agent and presents the following structure:

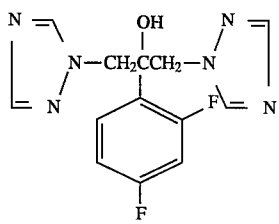

Canadian Letters Patent No. 1,170,263 [corresponding to U.S. Pat. No. 4,416,682 and European Patent Application Serial No. 0044605 (published Jan. 27, 1982)] purports to teach compounds having the following structure:

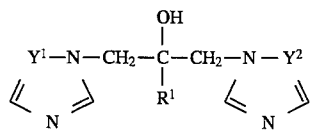

wherein $y^1$ and $y^2$ may be =N-, and $R^1$ may be aryl (page 1, line 16) wherein aryl may be substituted by "halogen (e.g., fluorine, chlorine or bromine)" (page 2, lines 17–18) and processes for the manufacture thereof (see for example page 7, line 1 to page 9, line 21).

One of the molecules:

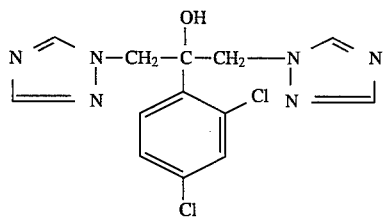

1,3-Bis-(1,2,4-triazol-1-yl)-2-2,4-dichloro-phenyl)-propan-2-ol is alleged to be teratongenic (alleged at page 3, line 17 of Canadian Letters Patent No. 1,181,076):

... foetuses from animals treated with the compound in which R=2,4-Dichlorophenyl at 20 mg/kg body weight showed malformations, in particular cleft palates. Examination of visceral and skeletal features revealed that this compound was teratogenic at doses as low as 1 mg/kg, e.g., presence of microphthalmia, increased incidence of dilation of the ureters and renal pelves, delay in ossification of some bones, and increased incidence of a $14^{th}$ pair of ribs.

Also, the compound in which R=4-Chlorophenyl was extremely embryotoxic at 20 mg/kg, whilst the compound in which R=2-Chlorophenyl produced external abnormalities (cleft palate) at this dose. These compounds are specifically disclosed as "Compounds 1 and 9," respectively, in Table 1 of the ICI applications. In addition, the compounds in which R=3-Chlorophenyl and R=4-Bromophenyl, which are claimed but not specifically disclosed in the ICI applications, also produced the same external abnormalities at 20 mg/kg. The latter compounds was also embryotoxic at this dose (page 4, line 16- page 5, line 9).

It is clear that, if true, this useless compound is claimed to be one of the compounds of the purported invention of Canadian Letters Patent No. 1,170,263.

The said Canadian Letters Patent No. 1,170,263 and corresponding U.S. patent and European application referred to above disclose processes for the manufacture of Fluconazole, wherein $R^1$ is aryl substituted by the halogen (fluorine) and $Y^1$ and $Y^2$ is =N-.

Canadian Letters Patent No. 1,181,076 discloses only Fluconazole and was actually filed in Canada on Jun. 4, 1982. European Patent Application Serial No. 0044605 (corresponding to Canadian letters Patent No. 1,170,263) was published 27.01.82. Canadian Letters Patent No. 1,181,076 discloses the same processes as does Canadian Letters Patent No. 1,170,263 and European Patent Application Serial No. 0044605.

Canadian Letters Patent No. 1,182,822 relates to an intermediate for making Fluconazole. Several methods for the synthesis of Fluconazole are reported in the literature (EP 0096569; ES 9002961; CA 1,191,076; CA 1,182.822; CA 1,170,263; ES 9502961; GB 2099818; US 4,404,216; ES 549020; ES 549684; ES 549022; ES 549021; EP 83-303244) and some prominent ones are listed below:

(a) The reaction of 1,2,4-Triazole with compound of formula II-B gives Fluconazole. Compound II was prepared according to the following scheme (Canadian Letters Patent No. 1,181,076):

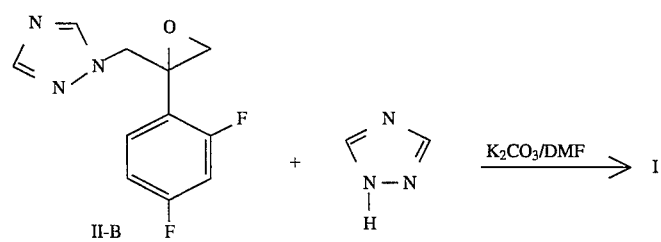

-continued

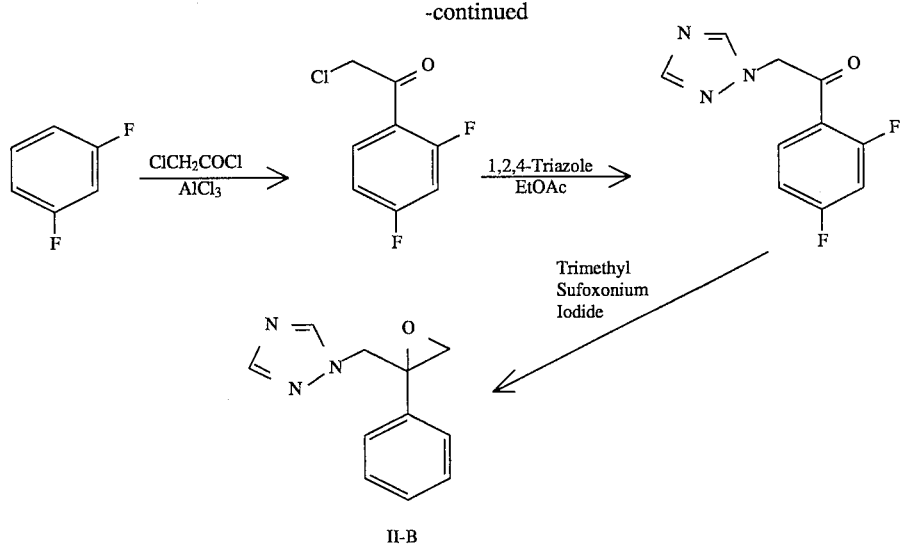

II-B

This method involves conversion of epoxide (II-B) to Fluconazole (44% yield). Epoxide (II-B) was prepared from commercially-available 1,3-Difluorobenzene over three steps. Although the chemistry involved is not too difficult, the yields obtained in Steps 2–4 are very low. The overall yield in this process Difluororbenzene → Fluconazole is about 4–8%.

(b) Fluconazole is also obtained by reacting 1,2,4-Triazole with a compound of formula III-B, which in turn is prepared according to the following scheme. Alternatively, Compound I can be obtained by the reaction of 1,3-ditriazole acetone with the corresponding Grignard of Difluorobenzene (CA 1,182,822; CA 1,181,076; ES 549020).

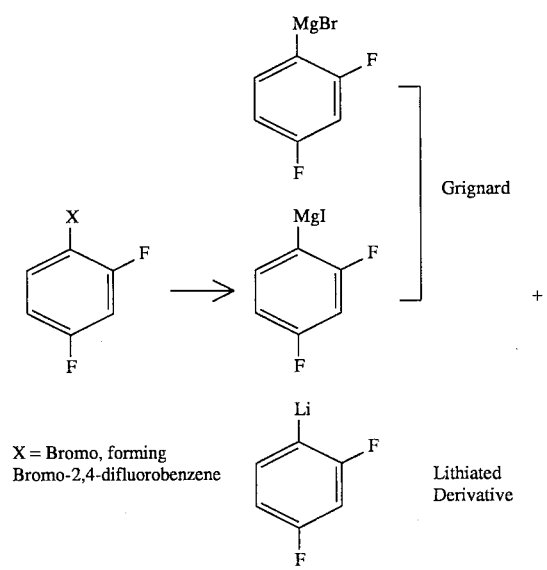

X = Bromo, forming Bromo-2,4-difluorobenzene

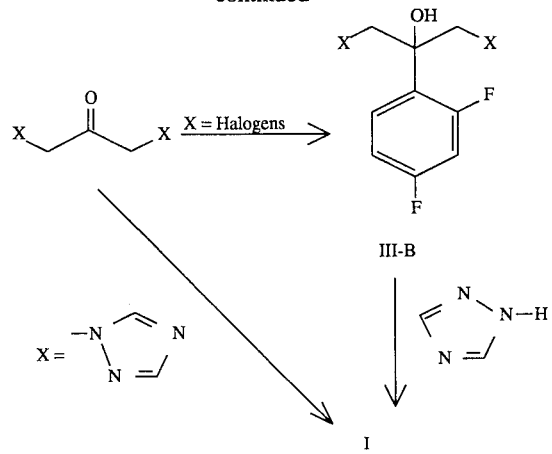

In this process, 1-Bromo-2,4-difluorobenzene is converted to its corresponding 1-lithiated derivative or a Grignard. This intermediate is reacted with highly toxic and corrosive dihaloacetone to obtain the dihalo alcohol which is in turn converted to Fluconazole.

Lithiation of 1-Bromo-2,4-difluorobenzene involves the use of the highly sensitive (to moisture, air), highly flammable, and corrosive compound n-Butyl Lithium. Also, the solvents used in both lithiation and Grignard reactions are Diethyl Ether or Tetrahydrofuran. These solvents are extremely flammable and hazardous. The above-mentioned reagents and solvents are dangerous to handle in large quantities, and hence this method is not very attractive for largescale commercial production.

Compared to these two methods, Applicant's synthesis involves reaction conditions and reagent (raw materials) that are suitable for synthesis on a large scale. Better yields are obtained. The method achieves a total yield far greater than those percentages referred to previously (from the starting materials through the intermediates to the final product).

It is therefore an object of this invention to provide a new process for the manufacture of Fluconazole from starting materials which are readily available commercially, easily handled, relatively inexpensive, and relatively safe to use. The use of these starting materials produces such intermediates in high yields. Fluconazole is also produced in high yields. Thus, Fluconazole is produced by simple reactions in high yields, using commercially available inexpensive agents which are not hazardous.

It is therefore a further object of the invention to provide such processes which are more environmentally- and user-acceptable.

Further and other objects of the invention will be realized by those skilled in the art from the following summary of the invention and detailed description of embodiments thereof.

SUMMARY OF THE INVENTION

According to one aspect of the invention, a process for making Fluconazole is provided comprising the steps of:

In another preferred embodiment, the base $K_2CO_3$ and $H_2O$ is used in the step of manufacture of Compound I (Fluconazole) from Compound III.

According to another aspect of the invention, there is provided a process for making Fluconazole comprising the step of:

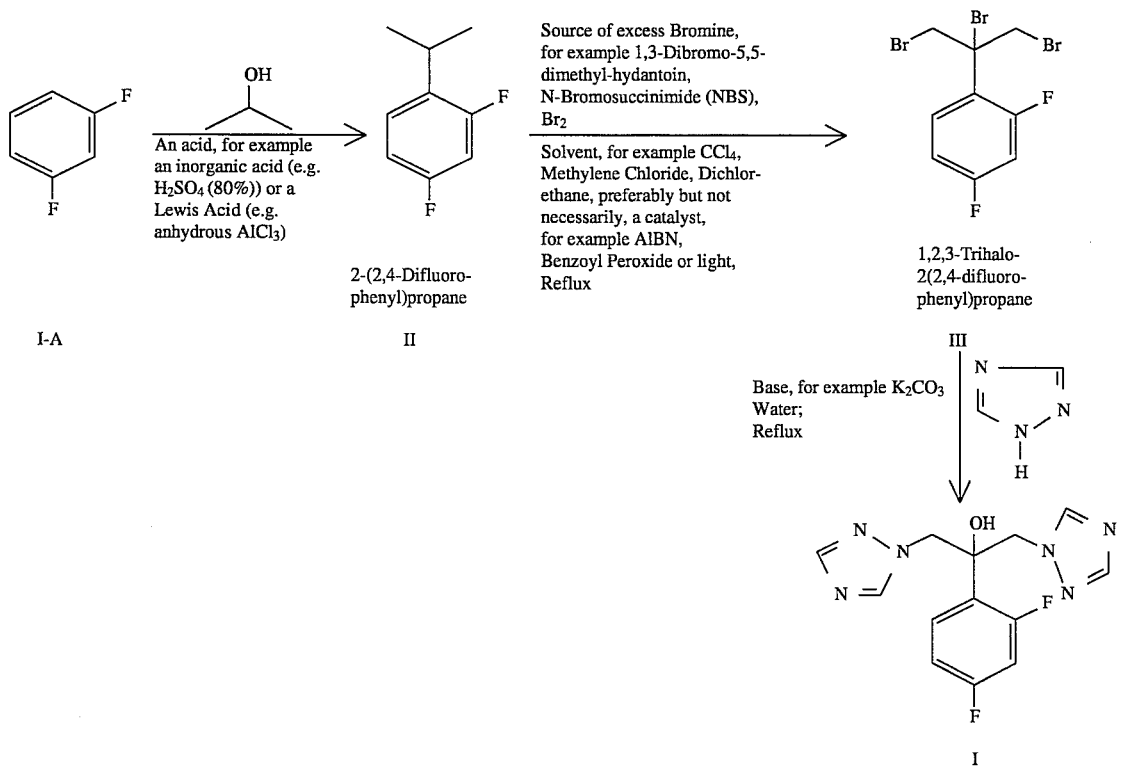

(AIBN is azobisisobutyronitrile)

The processes for making IA-II-III were disclosed in our earlier filed Canadian Patent Application Serial Number 2106032.

In a preferred embodiment, the step of manufacture of Compound II from Compound IA comprises heating to about 65° C. However, any suitable temperature may be used which will enable the reaction to proceed.

In yet another preferred embodiment, the step of manufacture of Compound II from Compound I-A comprises the use of an inorganic acid, for example $H_2SO_4$ (in the order of about 80%). Other suitable acids comprise a Lewis Acid, for example anhydrous $AlCl_3$.

In a further preferred embodiment, the source of bromine is 1,3-Dibromo-5,5-dimethylhydantoin in the step of manufacture of Compound III from Compound II. Other sources may be $Br_2$ and N-Bromosuccinimide.

In another embodiment, Dichloroethane is used as the solvent in the step of manufacture of Compound III from Compound II. Other suitable solvents may comprise Methylene Chloride and Carbon tetrachloride ($CCl_4$).

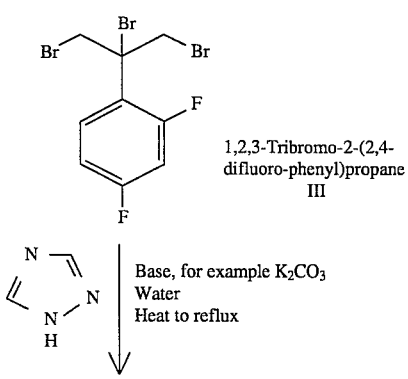

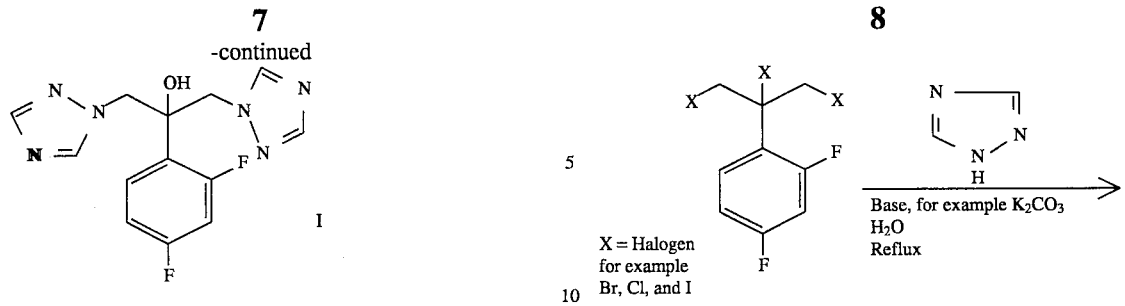

Even though the reaction proceeds in "one pot" (one vessel), the process may proceed through the formation of a Dibromo-hydroxy compound formed by the hydrolysis of the Benzylic Bromide before production of Fluconazole.

In a preferred embodiment, said process further comprises heating to reflux for about 15–16 hours, cooling to about room temperature, and extracting Compound I with EtOAc.

According to another aspect of the invention, there is provided a process for making Fluconazole comprising the steps of:

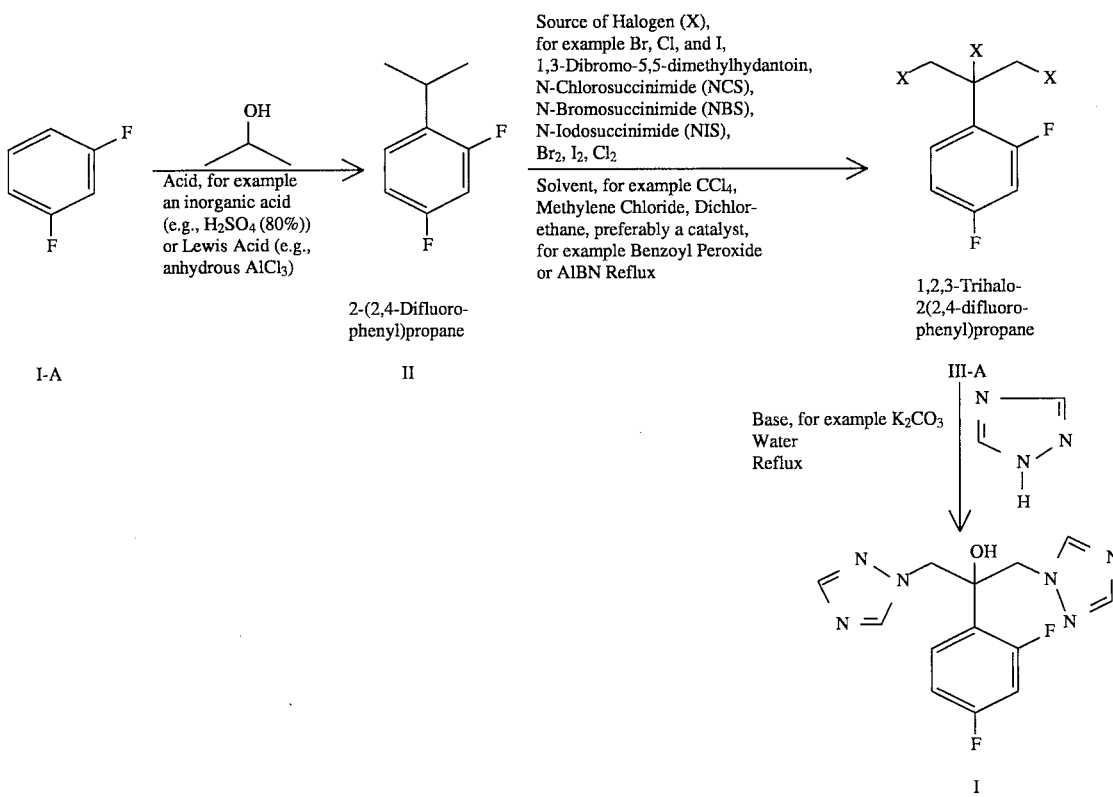

In an embodiment, the source of halogen (X) 1,3-Dibromo-5,5-dimethylhydantoin.

In another embodiment, an appropriate base in the step of manufacturing Compound I from Compound III-A is $K_2CO_3$.

The processes from IA→MI→IIIA are disclosed in earlier filed Canadian Patent Application Serial number 2106032.

In another embodiment, the step of manufacturing Compound I from Compound III-A further comprises the addition of $H_2O$.

According to another aspect of the invention, there is provided a process for making Fluconazole comprising the step of:

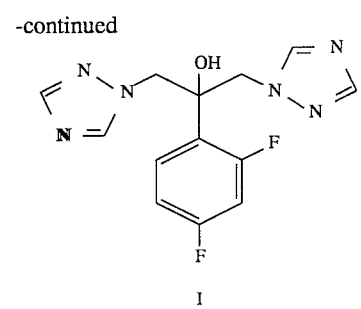

In a preferred embodiment said reflux is carried out for about 15–18 hours with vigorous stirring.

According to yet another aspect of the invention there is provided a process of mixing 1,2,3-Tribromo-2-(2,4-difluorophenyl) propane and water with 1,2,4-Triazole and K₂CO₃ to produce Fluconazole.

The following examples are provided:

EXAMPLE 1

2-(1,3-Difluorophenyl)propane II

To a rapidly stirred mixture of 1,3-Difluorobenzene (31.5 ml, 320 mmol) and 80% H₂SO₄ (150 ml), Isopropanol (25 ml, 320 mmol) was added at room temperature. The mixture was heated to 65° C. and stirred for four hours. The resulting light brown mixture was cooled to room temperature. The organic layer was separated from the H₂SO₄ and washed twice with 50 ml saturated NaCl (aqueous). The organic layer was subjected to fractional distillation to give 55.2% (27.6 g, 177 mmol) of the title compound and 27.1% (9.9 g, 86.8 mmol) recovered 1,3- Difluorobenzene.

bp: 147°–148° C.

¹H NMR (CDCl₃, 60 MHz),∂1.25 (6H,d,J=7 Hz),3.19 (1H, septet,J=7 Hz),6.50– 6.90 (2H,m),6.90–7.30 (1H,m).

EXAMPLE 2

1,2,3-Tribromo-2-(2,4-difluorophenyl)propane III

To a solution of 2-(2,4-Difluorophenyl)propane II (100 g, 0.64 mol) in 1.5 L of Dichloroethane, 1,3-Dibromo-5,5-dimethylhydantoin) (200 g, 0.7 mol) was added. After the mixture was heated to reflux 5–6 hours, half of the volume of the Dichloroethane was distilled off and the reaction was cooled down to room temperature. 1,3-Dibromo-5,5-dimethylhydantoin (92 g, 0.32 mol) and a catalytic amount of Benzoyl Peroxide (1.244 g, 0.08 mol %) were added and continued refluxing for 24 hours. The reaction mixture was cooled down to room temperature and filtered. The filtrate was washed with 2N HCl (500 ml), 10% Sodium Thiosulfate (500 ml) and water (500 ml) respectively. The organic layer was dried (Na₂SO₄) and the CCl₄ was evaporated in vacuo to yield essentially pure title compound.

¹H NMR (CDCl₃ 60 MHz),∂14.36 (4H,s),6.60–7.10 (2H, m),7.2–7.25 (1H,m).

EXAMPLE 3

2-(2,4-Difluorophenyl)-1,3-bis(1H-1,2,4-triazole-1-yl) propane (I)

To a mixture of 1,2,3-Tribromo-2-(2,4-difluorophenyl) propane (5 g, 12.7 mmol) and water (25 ml), 1,2,4-Triazole (3.5 g, 50.8 mmol) and K₂CO₃ (3.5 g, 25.5 mmol) were added. The mixture was heated to reflux for 15-18 hours with vigorous stirring. The reaction mixture was cooled to room temperature and the product was extracted with EtOAc (3×100 ml). The combined EtOAc phase was washed with water and dried (Na₂SO₄). Evaporation of the solvent in vacuo and purification of the residue on a silica gel column with EtOAc and EtOH:EtOAc (1:19) as the elements, furnished the title compound (0.88 g, 23%).

As many changes can be made to the embodiments of the invention without departing from the scope of the invention, it is intended that all material contained herein be interpreted as illustrative of the invention and not in a limiting sense.

THE EMBODIMENTS OF THE INVENTION IN WHICH AN EXCLUSIVE PROPERTY OR PRIVILEGE IS CLAIMED ARE AS FOLLOWS:

1. A process for making Fluconazole comprising the step of reacting:

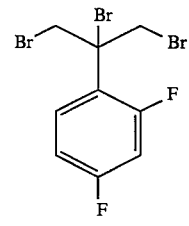

III

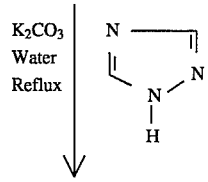

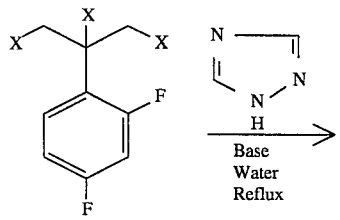

I

2. A process for making Fluconazole comprising the step of:

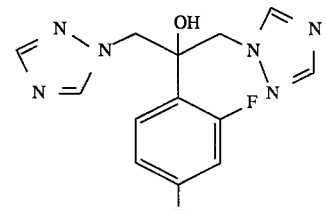

wherein X is a Halogen

III-A

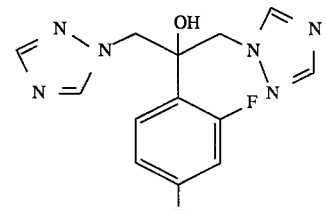

IV

3. The process of claim 2, wherein the base is K₂CO₃.

4. The process of claim 2 or 3, wherein said reflux is carried out for about 15–18 hours with vigorous stirring.

* * * * *